(12) United States Patent
Mintzer et al.

(10) Patent No.: US 10,150,914 B2
(45) Date of Patent: Dec. 11, 2018

(54) CERAMIC PHOSWICH WITH FUSED OPTICAL ELEMENTS, METHOD OF MANUFACTURE THEREOF AND ARTICLES COMPRISING THE SAME

(71) Applicant: Siemens Medical Solutions USA, Inc., Malvern, PA (US)

(72) Inventors: Robert A. Mintzer, Knoxville, TN (US); Peter Carl Cohen, Knoxville, TN (US); Mark S. Andreaco, Knoxville, TN (US); Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 148 days.

(21) Appl. No.: 14/951,921

(22) Filed: Nov. 25, 2015

(65) Prior Publication Data

US 2017/0145307 A1    May 25, 2017

(51) Int. Cl.
  *C09K 11/77*     (2006.01)
  *G21K 4/00*      (2006.01)
  (Continued)

(52) U.S. Cl.
  CPC .......... *C09K 11/7774* (2013.01); *C09K 11/77* (2013.01); *C09K 11/7706* (2013.01);
  (Continued)

(58) Field of Classification Search
  CPC . C09K 11/7774; C09K 11/7792; C09K 11/77; G01T 1/2985; G21K 4/00; G21K 2004/02; G21K 2004/05
  See application file for complete search history.

(56) References Cited

U.S. PATENT DOCUMENTS 4,802,180 A * 1/1989 Brandle, Jr. ............ C30B 15/00
                                                    252/301.17
5,057,692 A * 10/1991 Greskovich ........... G01T 1/2023
                                                    250/361 R
(Continued)

FOREIGN PATENT DOCUMENTS

EP      1829950      9/2007
EP      2671940      12/2013
(Continued)

OTHER PUBLICATIONS

Phosphor Handbook; Shionoya and Yen, ed.; 1999; p. 178 and 193.*
(Continued)

*Primary Examiner* — C Melissa Koslow

(57) ABSTRACT

Disclosed herein is a scintillator comprising a plurality of garnet compositions in a single block having the structural formula (1):

$$M^1_a M^2_b M^3_c M^4_d O_{12} \quad (1)$$

where O represents oxygen, $M^1$, $M^2$, $M^3$, and $M^4$ represents a first, second, third and fourth metal that are different from each other, where the sum of a+b+c+d is about 8, where "a" has a value of 2 to 3.5, "b" has a value of 0 to 5, "c" has a value of 0 to 5 "d" has a value of 0 to 1, where "b" and "c", "b" and "d" or "c" and "d" cannot both be equal to zero simultaneously, where $M^1$ is rare earth element including gadolinium, yttrium, lutetium, or a combination thereof, $M^2$ is aluminum or boron, $M^3$ is gallium and $M^4$ is a codopant; wherein two compositions having identical structural formulas are not adjacent to each other and wherein the single block is devoid of optical interfaces between different compositions.

20 Claims, 3 Drawing Sheets

(51) Int. Cl.
  *G01T 1/20* (2006.01)
  *A61B 6/03* (2006.01)
(52) U.S. Cl.
  CPC ........ *C09K 11/7769* (2013.01); *G01T 1/2008* (2013.01); *G21K 4/00* (2013.01); *A61B 6/032* (2013.01); *A61B 6/037* (2013.01); *G21K 2004/02* (2013.01); *G21K 2004/06* (2013.01)

(56) References Cited

U.S. PATENT DOCUMENTS

| | | | | |
|---|---|---|---|---|
| 6,361,735 | B1* | 3/2002 | Venkataramani | B28B 1/008 156/89.11 |
| 6,630,077 | B2* | 10/2003 | Shiang | G01T 1/2023 250/363.04 |
| 7,019,284 | B2* | 3/2006 | Srivastava | C09K 11/628 250/256 |
| 8,461,535 | B2 | 6/2013 | Kuntz et al. | |
| 8,981,311 | B2 | 3/2015 | Levene et al. | |
| 2003/0015955 | A1 | 1/2003 | Shiiki et al. | |
| 2012/0218736 | A1* | 8/2012 | Zhang | B32B 18/00 362/84 |
| 2012/0225767 | A1 | 9/2012 | Imholt et al. | |

FOREIGN PATENT DOCUMENTS

| | | |
|---|---|---|
| EP | 2826835 | 1/2015 |
| JP | 2012177134 A | 9/2012 |
| JP | 2013002882 A | 1/2013 |
| RU | 2388017 | 4/2010 |
| WO | 2013136804 A1 | 9/2013 |
| WO | 2015106904 | 7/2015 |

OTHER PUBLICATIONS

Extended European Search Report for Corresponding European Patent Application No. 16199787.9, dated Apr. 20, 2017.

Office Action for Corresponding Russian Patent Application No. 2016145925, dated Jun. 16, 2017. (English translation attached).

Wu, et al., "Spectral Properties of Various cCerium Doped Garnet Phosphors for Application in White Gan-based LEDS," Materials Research Society Symposium Proceedings, Pittsburg, PA; vol. 658, Jan. 1, 2001.

Aleksanyan et al.; "Investigation of luminescence processes in YAG single crystals irradiated by 50 MeV electron beam"; Radiation Measurements 56; 2013, pp. 54-57.

Kirm et al.; "Dependence of the efficiency of various emissions on excitation density in BaF2 crystals"; Radiation Measurements 33; 2001, pp. 515-519.

Kirm et al.; "Relaxation of Electronic Excitations in Csl Crystals Studied by Synchrotron Radiation and Pulsed Electrons", Radiation Measurements vol. 29, No. 34, 1998, pp. 257-261.

Mares et al.; "Scintillation response of Ce-doped or intrinsic scintillating crystals in the range up to 1 MeV"; Radiation Measurements 38; 2004, pp. 353-357.

Murk et al.; "Complex Oxides: Electron Excitations and Their Relaxation"; Radiation Measurements, vol. 24, No. 4.; 1995, pp. 371-374.

Padlyak et al.; "Nature of intrinsic luminescence in the glasses of CaO—Ga2O3—GeO2 system"; Radiation Measurements 38; 2004, pp. 593-597.

Rodnyi; "Progress in fast scintillators"; Radiation Measurements 33; 2001, pp. 605-614.

Sako et al.; "A detailed study on Gd2SiO5 scintillators: recovery from increased photon yield following irradiation"; IOP Publishing for Sissa Medialab; Jun. 24, 2015, 13 pages.

van Eijk; "Fast Scintillators and Their Applications"; Nucl. Tracks Radiat. Meas., vol. 21, No. 1; 1993, pp. 5-10.

Office Action dated Nov. 27, 2017 in KR Patent Application No. 10-2016-0156566 (English translation attached).

Kamada, et al., "Composition Engineering in Cerium-Doped (Lu,Gd)3(Ga,Al)5,O12 Single-Crystal Scintillators", Cryst. Growth Des. 2011, 11, 4498-4490.

JP office action dated Apr. 24, 2018 in JP Application No. 2016-227828, 10 pages (English translation attached).

* cited by examiner

CERAMIC PHOSWICH WITH FUSED OPTICAL ELEMENTS, METHOD OF MANUFACTURE THEREOF AND ARTICLES COMPRISING THE SAME

BACKGROUND

Disclosed herein is a ceramic phoswich with fused optical elements, method of manufacture thereof and articles comprising the same.

In radiation detection applications, it is often desirable to extract depth of interaction information from the detection media. This improves the localization of gamma particles interacting within a solid. A common method allowing one to extract this information is by using a phoswich configuration where two or more scintillators are bonded together into a single functional unit. The scintillation materials used to build a phoswich have distinct scintillation characteristics (for example different scintillation decay times, or different wavelengths) that can be used to determine which section of the phoswich interacted with a gamma particle. Since scintillators used in the phoswich configuration are optically coupled to each other by using an optical coupling material with a significantly lower index of refraction than those of the dense scintillators, significant amounts of scintillation photons are reflected or lost at the scintillator interface with the optical coupling material. This causes significant degradation of the detector energy and time resolution.

SUMMARY

Disclosed herein is a scintillator comprising a plurality of garnet compositions in a single block having the structural formula (1):

$$M^1_a M^2_b M^3_c M^4_d O_{12} \quad (1)$$

where O represents oxygen, $M^1$, $M^2$, $M^3$, and $M^4$ represents a first, second, third and fourth metal that are different from each other, where the sum of a+b+c+d is about 8, where "a" has a value of about 2 to about 3.5, "b" has a value of 0 to about 5, "c" has a value of 0 to about 5 "d" has a value of 0 to about 1, where "about" is defined as ±10% deviation from the desirable value, where "b" and "c", "b" and "d" or "c" and "d" cannot both be equal to zero simultaneously, where $M^1$ is a rare earth element including but not being limited to gadolinium, yttrium, lutetium, scandium, or a combination of thereof, $M^2$ is aluminum or boron, $M^3$ is gallium and $M^4$ is a dopant and comprises one of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium; wherein two compositions having identical structural formulas are not adjacent to each other and wherein the single block is devoid of optical interfaces between different compositions.

Disclosed herein too is a method comprising disposing a plurality of compositions adjacent to each other; where the plurality of compositions each have the structural formula (1):

$$M^1_a M^2_b M^3_c M^4_d O_{12} \quad (1)$$

where O represents oxygen, $M^1$, $M^2$, $M^3$, and $M^4$ represents a first, second, third and fourth metal that are different from each other, where the sum of a+b+c+d is about 8, where "a" has a value of about 2 to about 3.5, "b" has a value of 0 to about 5, "c" has a value of 0 to about 5 "d" has a value of 0 to about 1, where "b" and "c", "b" and "d" or "c" and "d" cannot both be equal to zero simultaneously, where $M^1$ is rare earth element including but not being limited to gadolinium, yttrium, lutetium, scandium, or any combination of thereof, $M^2$ is aluminum or boron, $M^3$ is gallium and $M^4$ is a dopant and comprises one of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium; wherein two compositions having identical structural formulas are not adjacent to each other; compressing the compositions into one another; and annealing the compositions to form a single block that is devoid of optical interfaces between different compositions.

DETAILED DESCRIPTION

Figure 1:
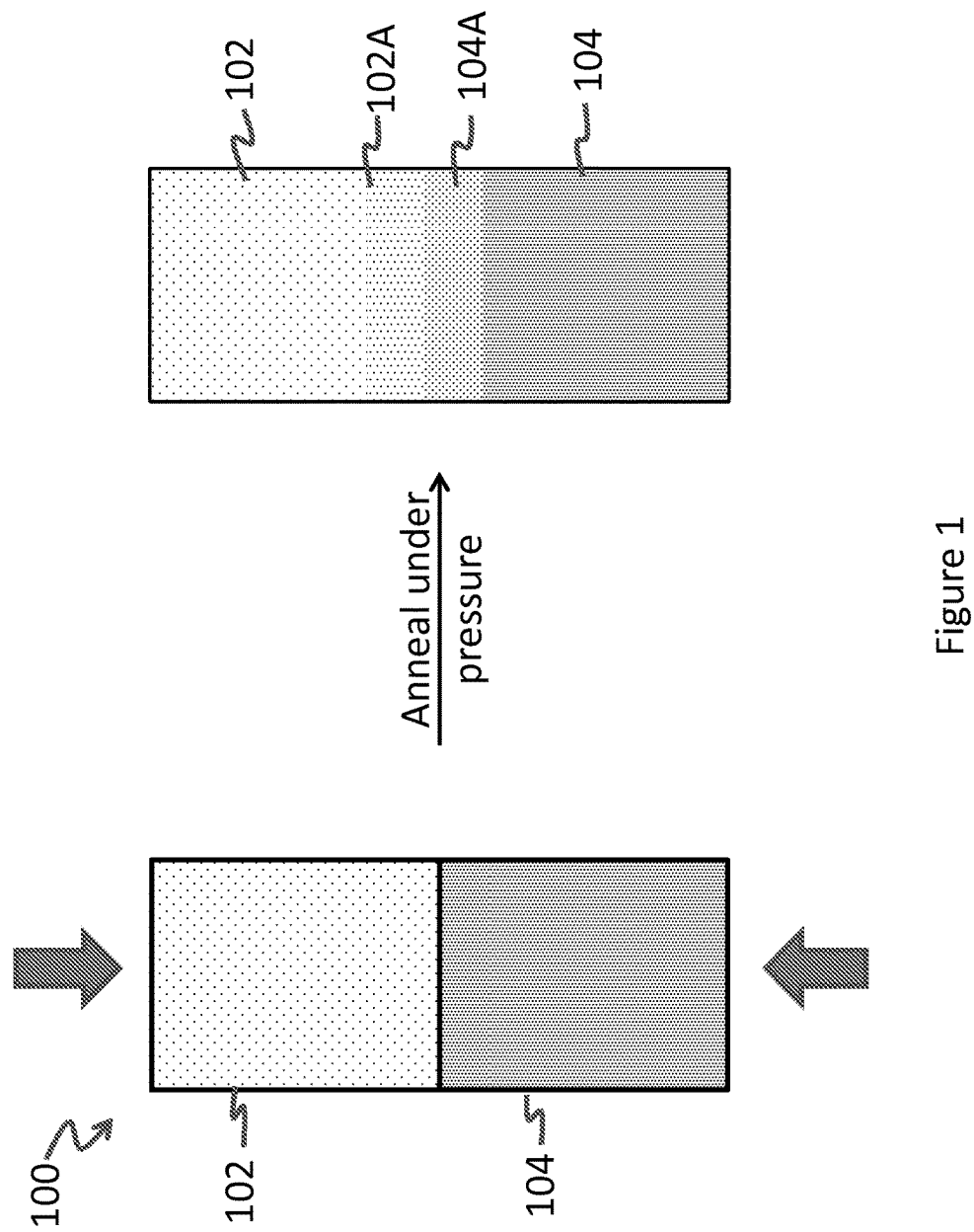
FIG. 1 is a depiction of one exemplary method of manufacturing the scintillator phoswich disclosed herein.

Disclosed herein is a scintillator phoswich having two or more garnet compositions that are different from each other. The garnet compositions have a gradually varying composition (e.g., a gradient) at the interface between the two or more garnet compositions and this gradually varying composition precludes the presence of an optical interface between the two or more compositions. As a result of having a gradually varying composition instead of a sharp interface between the two or more different compositions there are no losses due to reflection at the interface boundary. In an embodiment, the refractive index values at the boundaries between different garnet compositions change gradually from one garnet composition to the other. An optical interface is one where there is an abrupt discontinuity in the index of refraction because of the use of an optical coupling medium.

Disclosed herein too is a new method of creating a scintillator phoswich that is devoid of an interface boundary between two different compositions and that shows no losses due to reflection at what would have previously been the interface boundary between the two compositions. The method comprises disposing two or more ceramic scintillator compositions in powder form adjacent to one another and then pressing these compositions together to produce a slab of powder. The slab of powder is then annealed (sintered) at an appropriate temperature that permits diffusion to occur between the different compositions and to produce the phoswich with a gradually varying composition between the different compositions. It may be noted that the combination of the application of heat (during annealing) and compressive pressure lead to the grain growth phenomena. The application of heating and compressive pressure is also termed "sintering". The compositions may therefore considered to be sintered into a single block of material.

The method results in two or more garnet scintillator ceramics present in one seamless integrated medium during the process of pressing without creating any distinct optical interface(s). While the details herein are focused mostly on powder compositions, the scintillator phoswich's can also be produced from gels and from emulsions. These are detailed briefly towards the end of this disclosure.

Garnet scintillators have recently increased in popularity due to significant improvements in scintillation efficiency and good control over decay time. An additional advantage of garnets is their tunability that permits significant modifications of their scintillation characteristics while maintaining good crystal phase stability. Their cubic symmetry allows one to make optically transparent ceramics. Ceramic technology provides new opportunities for making complex phoswich structures. It allows precise control of the uniformity and stoichiometry of the material as well as eliminating incongruency issues that sometimes occur during standard crystal growth from the melt. Garnet ceramics appear to be very well suited for this technology.

The method of making a ceramic phoswich is by fusing two or more ceramics in one seamless integrated medium during the process of pressing without creating any distinct optical interfaces. FIG. 1 shows a block of powder 100 having two different powdered garnet scintillator compositions (hereinafter powdered compositions) 102 and 104 that are placed adjacent to one another in a mold (not shown) and pressurized to form a block of the powder. It is to be noted that while the FIG. 1 depicts only two different compositions, it is possible to have 3 or more, 4 or more and 5 or more different compositions. In short, it is possible to perform the method detailed herein on a plurality of different compositions that are placed adjacent to one another. In an embodiment, the different powdered compositions may be placed on top of one another in a mold.

The powdered compositions may be purchased commercially. It is desirable for the compositions to be as pure as possible, preferably having a purity of 99% or greater, preferably 99.9% or greater and more preferably 99.99% or greater, based on the total weight of the powdered composition. The particles or powder have an average particle size that range from 1 nanometers to 500 micrometers, preferably 5 nanometers to 50 micrometers, and more preferably 10 nanometers to 20 micrometers. The radius of gyration of the particles is measured to determine average particle size. Light scattering or electron microscopy may be used to determine the particle size.

The powders may be optionally further pulverized in a ball mill, roll mill or other pulverizing device. The pulverized powders may then be subjected to an optional sieving process if it is desirable to use particles of a particular size.

The powdered compositions are then subjected to pressure and annealing at a temperature effective to bring about diffusion of the molecules of the different composition into one another. The pressure is preferably a compressive force as indicated by the direction of the arrows in the FIG. 1. In an embodiment, the pressure and the annealing can be applied simultaneously or sequentially. If applied sequentially, the powdered composition is always subjected to pressure followed by the annealing. It is preferable that the powdered composition be subjected to pressure and to annealing simultaneously. The interface between the two compositions therefore contains a plurality of different progressively changing compositions from the first composition to the second composition.

Pressure is then placed on the powdered compositions in the mold to form a block of the powder. In an embodiment, the pressure is a compressive force of 1 MPa to 500 MPa.

The annealing is preferably conducted via convective or conductive heat transfer. In an embodiment, radiative heating (e.g. radiofrequency heating, microwave heating or infrared heating) may be conducted simultaneously or sequentially with the convective or conductive heating. In an embodiment, the heating is conducted via conduction while the sample is still in the press and under pressure.

The annealing is conducted at a temperature of 500 to 1750° C., preferably 850 to 1700° C. in an oxygen containing atmosphere. Atmospheres other than an oxygen atmosphere may also be used if desired.

With reference now to the FIG. 1 again, during annealing, molecules from the two different powdered compositions 102 and 104 diffuse towards each other to produce a gradient indicated by the numerals 102A and 104A. During annealing, grain boundary growth occurs in the powders and the respective grains from the powdered compositions 102 and 104 fuse into each other resulting in the disappearance of optical interface that normally separate sections of the phoswich. The small differences of refractive index will transition smoothly between layers causing scintillation photons to be affected only slightly at the interface, and not suffer from a high probability of reflections that would occur at the distinct optical boundaries resulting from the use of an optical coupling medium.

In an embodiment, the regions 102A and 104A have an intermediate composition that lies between the powdered compositions 102 and 104. The presence of the intermediate compositions results in a seamless integrated medium between the powdered compositions 102 and 104 without any distinct optical interface(s).

In an embodiment, the plurality of garnet compositions that are placed adjacent to each other prior to the application of pressure are gadolinium-gallium containing garnets that have the structural formula:

$$M^1_a M^2_b M^3_c M^4_d O_{12} \qquad (1)$$

where O represents oxygen, $M^1$, $M^2$, $M^3$, and $M^4$ represents a first, second, third and fourth metal that are different from each other, where the sum of a+b+c+d is about 8, where "about" is defined as ±10% deviation from the desirable value, where "a" has a value of about 2 to about 3.5, preferably about 2.4 to about 3.2, and more preferably about 3.0, "b" has a value of 0 to about 5, preferably about 2 to about 3, and more preferably about 2.1 to about 2.5, where "b" and "c", "b" and "d" or "c" and "d" cannot both be equal to zero simultaneously, where "c" has a value of 0 to about 5, preferably about 1 to about 4, preferably about 2 to about 3 and more preferably about 2.1 to about 2.5, "d" has a value of 0 to about 1, preferably about 0.001 to about 0.5 and more preferably about 0.003 to about 0.3. The term "about" represents a deviation of ±10% from a given value.

In the formula (1) above, $M^1$ is rare earth element including but not being limited to gadolinium, yttrium, lutetium, scandium, or any combination of thereof. $M^1$ is preferably gadolinium and yttrium, $M^2$ is aluminum or boron, $M^3$ is gallium and $M^4$ is a dopant and comprises one or more of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium.

$M^1$ is preferably gadolinum. For $M^1$, some of the gadolinium can be substituted with one or more of yttrium, gadolinium, lutetium, lanthanum, terbium, praseodymium, neodymium, cerium, samarium, europium, dysprosium, holmium, erbium, ytterbium, scandium, or combinations thereof. In an embodiment, some gallium can be substituted with yttrium. $M^3$ is preferably aluminum.

In an embodiment, the dopant $M^4$ includes Tl+, Cu+, Ag+, Au+, Pb2+, Bi3+, In+, Sn2+, Sb3+, Ce3+, Pr3+, Eu2+, Yb2+, Nb5+, Ta5+, W6+, Sr2+, B3+, Ba2+, Mg2+, Ca2+, or combinations thereof.

In an embodiment, the first powdered composition 102 will have a first structural formula (1), while the second powdered composition 104 will have a second structural formula (1) that is different from the first structural formula. In other words, the first powdered composition is chemically different from the second powdered composition. In this manner, "n" different compositions each having a different composition (in terms of structural formula (1)) from its nearest neighbor may be placed adjacent to one another and then subjected to pressure and annealing to form the garnet with no reflective interfaces. The number "n" can be an integer having a value of up to 100, 2 to 30 or more, 3 to 10 or more, and 4 to 6 or more.

It is indeed possible to have multiple portions of the resulting garnet having an identical structural formula (1), so long as the two identical compositions are not placed next to one another. This is shown in the FIG. 2(A), where the powdered compositions 102 and 104 are repeatedly placed in alternating sequences adjacent to one another. In another embodiment depicted in the FIG. 2(B), the resulting garnet can have a series of powdered compositions 102, 103, 104, 105, 106, and so on, placed adjacent to one another, where each composition is different from its neighboring composition and no compositions are ever repeated. Many such variations are possible and while all of these are not detailed here they are envisioned to be within the scope of the disclosure.

Figure 2A:
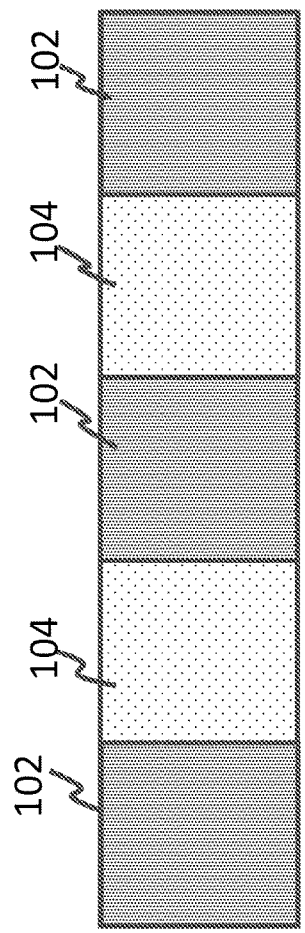
FIG. 2(A) depicts one exemplary scintillator phoswich.
Figure 2B:
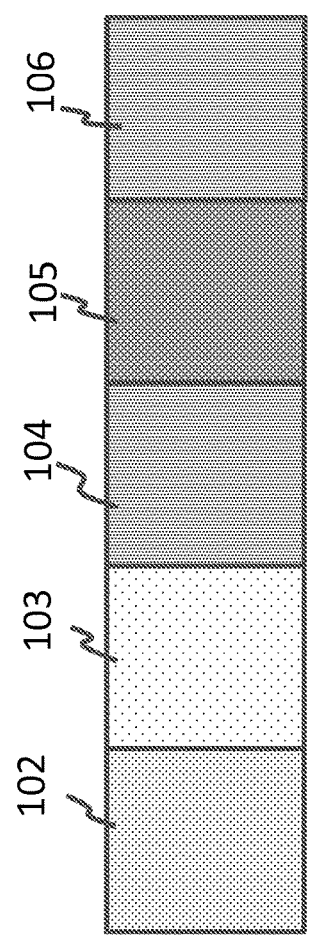
FIG. 2(B) depicts another exemplary scintillator phoswich.
Figure 3:
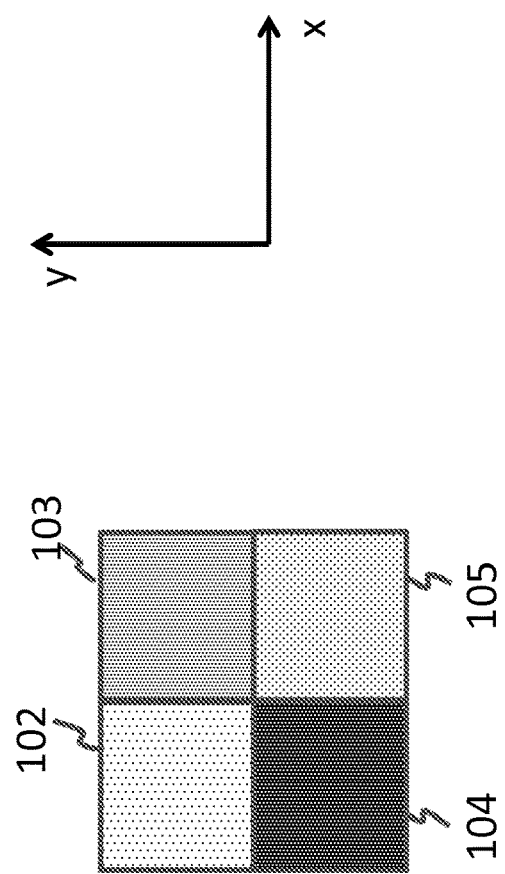
FIG. 3 depicts another exemplary scintillator phoswich where the neighboring compositions are added on to one another in a plurality of directions.

While the FIGS. 1, 2(A) and 2(B) show the different powdered compositions arranged alongside each other in a single direction (i.e., horizontally), they can be arranged to be adjacent to each other in multiple directions, such as, for example, the x-direction, the y-direction and/or the z-direction. FIG. 3 depicts an embodiment where the resulting garnet has different compositions arranged in two different directions. In some embodiments, the different directions may be at right angles to each other. In other embodiments, the different directions are at angles that are greater or less than 90 degrees from each other. Angles can be measured by lines connecting the center of mass of the different compositions.

In manufacturing a garnet scintillator from two different powdered compositions it is desirable but not necessary for the two different compositions to contain identical elements in different ratios. For example, the first powdered composition and the second powdered composition can both comprise gadolinium, aluminum and gallium (such compositions are commonly denoted by the acronym GAGG), but in differing ratios from each other. For example, the first powder composition may be $Gd_3Al_2Ga_3O_{12}$ and the second powder composition may be $Gd_3Al_3Ga_2O_{12}$ with different levels of Ce3+ activator. In another embodiment, the first powder composition comprises $Gd_{2.5}Y_{0.5}Al_2Ga_3O_{12}$ while the second powder composition comprises $Gd_{2.5}Y_{0.5}Al_3Ga_2O_{12}$.

In another embodiment, the first powder composition may be a GAGG composition—i.e., one of $Gd_3Al_2Ga_3O_{12}$ or $Gd_3Al_3Ga_2O_{12}$, while the second powder composition may be a GYGAG (where GYGAG stands for gadolinium-yttrium-gallium-aluminum garnet) such as, for example, $Gd_{1.5}Y_{1.5}Ga_{2.5}Al_{2.5}O_{12}$.

The first powder composition and the second powder composition may thus be selected from the group consisting of GAGG—gadolinium-aluminum-gallium garnet, GYGAG—gadolinium-yttrium-gallium-aluminum garnet, GSGG—gadolinium-scandium-gallium-garnet, GLAGG—gadolinium-lutetium-aluminum-gallium garnet, or the like.

While the aforementioned method details manufacturing the scintillator phoswich from powder compositions, these phoswich's may also be manufactured using a sol-gel approach, or an emulsion-based approach. In the sol-gel approach, both the first composition and the second composition can comprise gels having the desired garnet composition. The gels are manufactured from a sol, typically prepared from metal alkoxides, metal halides, and the like. An acidic or basic catalyst may be used to facilitate a reaction between the metal alkoxides. A solvent such as, for example, an alcohol may be used to compatibilize the different metal alkoxides.

For example, the GAGG compositions detailed above can be prepared into a gel using gadolinium isopropoxide, aluminum-sec-butoxide and gallium ethoxide all of which are metal alkoxides available in liquid form. The first gel composition and the second gel composition can then be placed adjacent to each other and the temperature gradually increased under pressure to produce the scintillator phoswich that is devoid of an interface boundary between two different compositions. Supercritical extraction may be employed to remove solvents and byproducts from the resulting scintillator phoswich, while producing a suitably sized monolith.

It is to be noted that this disclosure encompasses the manufacturing of scintillator phoswich's from a combination or powders and gels. The powders and gels can be placed adjacent to each other or can be mixed together to form a powder-gel composition, where a plurality of powder-gel compositions can be placed adjacent to each other and pressed and annealed to form the scintillator phoswich.

The respective compositions after fabrication are in the form of a single block of scintillator phoswich material. In an embodiment, the single block of scintillator phoswich material is a monolith without any interfaces or coupling devices. The scintillator phoswich may have a length of 1 to 10 centimeters and transverse dimensions of 1 millimeter to 10 centimeters or more. In an embodiment, the transverse dimensions may be "pixel sized", in the range of 1 millimeters to 10 centimeters (in monolithic block configuration arrangements), 1 millimeter to 6 millimeters (for example pixels of a "clinical", i.e., human subject, general purpose whole body, scanner), or 0.5 to 2 mm (pixels of a small animal research scanner, or a brain or other organ specific scanner); in any event, smaller than 1 centimeter.

In the emulsion-based approach, emulsions of the desired ingredients in emulsion form are mixed and catalyzed to produce the desired compositions. The emulsions after catalysis react to form gels, which are then treated as detailed above in the sol-gel approach to produce the desired scintillator phoswich. The disclosed method is advantageous in that it results in two or more garnet scintillator ceramics present in one seamless integrated medium during the process of pressing and sintering without creating any distinct optical interface(s).

In an embodiment, an article may have a scintillator that comprises a plurality of garnet compositions in a single block having the structural formula (1):

$$M^1_a M^2_b M^3_c M^4_d O_{12} \qquad (1)$$

where O represents oxygen, $M^1$, $M^2$, $M^3$, and $M^4$ represents a first, second, third and fourth metal that are different from each other, the sum of a+b+c+d is about 8, "a" has a value of about 2 to about 3.5, "b" has a value of 0 to about 5, "c" has a value of 0 to about 5, "d" has a value of 0 to about 1, where "b" and "c", "b" and "d" or "c" and "d" cannot both be equal to zero simultaneously, $M^1$ is a rare earth element comprising gadolinium, yttrium, lutetium, scandium, or any combination of thereof, $M^2$ is aluminum or boron, $M^3$ is gallium, and $M^4$ is a dopant and comprises one of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium; wherein two compositions having identical structural formulas are not adjacent to each other and wherein the single block is devoid of optical interfaces between different compositions. The article is a positron emission tomography (PET), or computed tomography (CT), or single photon emission computed tomography (SPECT) machine. In another embodiment, the scintillator phoswich's are used in positron emission tomography (PET), or computed tomography (CT), or single photon emission computed tomography (SPECT) machines and in other imaging devices.

The scintillator phoswich's are used in positron emission tomography (PET), or computed tomography (CT), or single photon emission computed tomography (SPECT) machines and in other imaging devices.

It is to be noted that all ranges detailed herein include the endpoints. Numerical values from different ranges are combinable.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A scintillator comprising:
a plurality of garnet compositions in a single block having the structural formula (1):

$$M^1_a M^2_b M^3_c M^4_d O_{12} \tag{1}$$

where
O represents oxygen,
$M^1$, $M^2$, $M^3$, and $M^4$ represents a first, second, third and fourth metal that are different from each other,
the sum of a+b+c+d is about 8,
"a" has a value of about 2 to about 3.5,
"b" has a value of 2 to about 5,
"c" has a value of 1 to about 5
"d" has a value of 0.001 to about 1,
where "b" and "c", "b" and "d" or "c" and "d" cannot both be equal to zero simultaneously,
$M^1$ is a rare earth element comprising gadolinium, yttrium, lutetium, scandium, or any combination of thereof,
$M^2$ is aluminum or boron,
$M^3$ is gallium, and $M^4$ is a dopant and comprises one of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium;
wherein two compositions having identical structural formulas are not adjacent to each other and
wherein the single block is devoid of optical interfaces between different compositions.

2. The scintillator of claim 1, where when $M^1$ is gadolinum, a portion of the gadolinium is substituted with one or more of yttrium, lutetium, lanthanum, terbium, praseodymium, neodymium, cerium, samarium, europium, dysprosium, holmium, erbium, ytterbium, scandium, or combinations thereof.

3. The scintillator of claim 1, where $M^2$ is aluminum.

4. The scintillator of claim 1, where
"a" has a value 2.4 to 3.2,
"b" has a value of 2 to 3,
"c" has a value of 1 to 4, and
"d" has a value of 0.001 to 0.5.

5. The scintillator of claim 1, where
"a" has a value of about 3,
"b" has a value of about 2.1 to about 2.5,
"c" has a value of about 2 to about 3 and
"d" has a value of about 0.003 to about 0.3.

6. The scintillator of claim 1, where the plurality of compositions are in powder form or gel form prior to an application of pressure to produce the block.

7. The scintillator of claim 1, where the plurality of garnet compositions comprise gadolinium-aluminum-gallium garnet, gadolinium-yttrium-gallium-aluminum garnet, gadolinium-scandium-gallium-garnet, and/or gadolinium-lutetium-aluminum-gallium garnet.

8. The scintillator of claim 1, where the scintillator comprises $Gd_3Al_2Ga_3O_{12}$ and $Gd_3Al_3Ga_2O_{12}$.

9. The scintillator of claim 1, where the scintillator comprises $Gd_{2.5}Y_{0.5}Al_2Ga_3O_{12}$ and $Gd_{2.5}Y_{0.5}Al_3Ga_2O_{12}$.

10. The scintillator of claim 1, where the plurality of compositions comprises n different compositions and where n is 2 to 100.

11. The scintillator of claim 1, where the plurality of compositions are arranged in 2 or more different directions.

12. An article having the scintillator of claim 1.

13. The article of claim 12, where the article is a positron emission tomography (PET), or computed tomography (CT), or single photon emission computed tomography (SPECT) machine.

14. A method comprising:
disposing a plurality of scintillator compositions adjacent to each other; where the plurality of scintillator compositions each have the structural formula (1):

$$M^1_a M^2_b M^3_c M^4_d O_{12} \tag{1}$$

where
O represents oxygen,
$M^1$, $M^2$, $M^3$, and $M^4$ represents a first, second, third and fourth metal that are different from each other,
the sum of a+b+c+d is about 8,
"a" has a value of about 2 to about 3.5,
"b" has a value of 2 to about 5,
"c" has a value of 1 to about 5,
"d" has a value of 0.001 to about 1,
where "b" and "c", "b" and "d" or "c" and "d" cannot both be equal to zero simultaneously, $M^1$ is a rare earth element comprising gadolinium, yttrium, lutetium, scandium, or a combination of thereof, $M^2$ is aluminum or boron, $M^3$ is gallium, $M^4$ is a dopant and comprises one of thallium, copper, silver, lead, bismuth, indium, tin, antimony, tantalum, tungsten, strontium, barium, boron, magnesium, calcium, cerium, yttrium, scandium, lanthanum, lutetium, praseodymium, terbium, ytterbium, samarium, europium, holmium, dysprosium, erbium, thulium or neodymium; wherein two scintillator compositions having identical structural formulas are not adjacent to each other;

compressing the scintillator compositions into one another; and annealing the scintillator compositions to form a single block that is devoid of optical interfaces between different scintillator compositions.

15. The method of claim 14, where the plurality of scintillator compositions adjacent to each other are in the form of powders, in the form of gels, or in the form of powders and gels prior to compressing the scintillator compositions into one another.

16. The method of claim 14, where the annealing and compressing are conducted simultaneously.

17. The method of claim 14, where when $M^1$ is gadolinium, a portion of gadolinium is substituted with one or more of yttrium, lutetium, lanthanum, terbium, praseodymium, neodymium, cerium, samarium, europium, dysprosium, holmium, erbium, ytterbium, scandium or a combination thereof.

18. The method of claim 14, where $M^1$ is gadolinium.

19. The method of claim 14, where the annealing is conducted at a temperature of 500 to 1750° C.

20. The method of claim 14, where the compressing is conducted at a pressure of 1 MPa to 500 MPa.

* * * * *